(12) United States Patent
Yoon

(10) Patent No.: US 9,739,785 B2
(45) Date of Patent: Aug. 22, 2017

(54) METHOD FOR ANALYZING PROTEIN-PROTEIN INTERACTION ON SINGLE-MOLECULE LEVEL IN CELL ENVIRONMENT, AND METHOD FOR MEASURING DENSITY OF PROTEIN ACTIVATED IN CYTOSOL

(71) Applicant: KOREA ADVANCED INSTITUTE OF SCIENCE AND TECHNOLOGY, Daejeon (KR)

(72) Inventor: Tae-Young Yoon, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/162,673

(22) Filed: May 24, 2016

(65) Prior Publication Data

US 2016/0266139 A1    Sep. 15, 2016

Related U.S. Application Data

(60) Division of application No. 14/059,294, filed on Oct. 21, 2013, now Pat. No. 9,377,462, which is a continuation of application No. PCT/KR2012/003087, filed on Apr. 20, 2012.

(30) Foreign Application Priority Data

Apr. 20, 2011   (KR) .................. 10-2011-0036942
Nov. 18, 2011   (KR) .................. 10-2011-0120653

(51) Int. Cl.
| | | |
|---|---|---|
| G01N 31/00 | (2006.01) | |
| G01N 33/53 | (2006.01) | |
| G01N 33/68 | (2006.01) | |
| G01N 21/64 | (2006.01) | |
| G01N 33/574 | (2006.01) | |
| G01N 21/77 | (2006.01) | |

(52) U.S. Cl.
CPC ..... *G01N 33/6845* (2013.01); *G01N 21/6428* (2013.01); *G01N 21/6486* (2013.01); *G01N 21/77* (2013.01); *G01N 33/574* (2013.01); *G01N 21/648* (2013.01); *G01N 21/6458* (2013.01); *G01N 2021/7786* (2013.01)

(58) Field of Classification Search
None
See application file for complete search history.

(56) References Cited

U.S. PATENT DOCUMENTS 9,377,462 B2 *   6/2016   Yoon .................. G01N 33/6845
9,423,400 B2 *   8/2016   Yoon .................. G01N 33/6845

FOREIGN PATENT DOCUMENTS

| JP | 09-222428 | | 8/1997 | |
| JP | WO 2005085801 | * | 9/2005 | ............. G01N 13/14 |
| JP | 2008-190879 | | 8/2008 | |

OTHER PUBLICATIONS

Javaherian et al. (Nucleic Acids Research, 2009, vol. 37, No. 8, e62, pp. 1-10).*
Petricoin et al. (Nature Reviews, Drug Discovery, vol. 1, Sep. 2002, pp. 683-695).*

* cited by examiner

*Primary Examiner* — Lisa Cook
(74) *Attorney, Agent, or Firm* — Lex IP Meister, PLLC

(57) ABSTRACT

A method of analyzing protein-protein interactions at a single molecular level is disclosed. The method of analyzing the interactions between first proteins and second proteins at the single molecular level includes: preparing at least two substrates, in which first protein-binding molecules that are biomolecules to be bound to the first proteins are attached to each of the substrates; inducing binding between the first proteins and the first protein-binding molecules on the first substrate and the second substrate, respectively, by supplying the first proteins included in the control group-cell to the first substrate among the two substrates and supplying the first proteins included in the experimental group-cell to the second substrate among the two substrates; supplying cell lysates of cells including the marker-tagged second proteins to the first substrate and the second substrate, respectively, when the first proteins and the first protein-binding molecules are bound to the first substrate and the second substrate, respectively; and comparing and analyzing the interactions between the first proteins and the second proteins on the first substrate and the second substrate in the supply of the cell lysates to the first substrate and the second substrate, respectively. For observing the interactions between the first proteins and the second proteins, the state of each cell and activation levels of the first proteins can be compared and analyzed by comparing after varying of a type of cells supplying the first proteins.

11 Claims, 13 Drawing Sheets

METHOD FOR ANALYZING PROTEIN-PROTEIN INTERACTION ON SINGLE-MOLECULE LEVEL IN CELL ENVIRONMENT, AND METHOD FOR MEASURING DENSITY OF PROTEIN ACTIVATED IN CYTOSOL

CROSS-REFERENCE TO RELATED APPLICATIONS

This application is a divisional application of U.S. patent application Ser. No. 14/059,294 filed on October 21 (now U.S. Pat. No. 9,377,462) and claims the benefit of U.S. patent application Ser. No. 14/059,294 (now U.S. Pat. No. 9,377,462), which are incorporated herein by reference.

TECHNICAL FIELD

The present invention relates to a method of analyzing protein-protein interactions and a method of measuring activated protein concentration in a cell lysate, and more specifically, to a method of analyzing protein-protein interactions, which can analyze the protein-protein interactions at a single molecular level in the actual intracellular environment, and also can compare and confirm each cell state and activation levels of first proteins by comparing after varying of a type of cell supplying the first proteins for observing interactions between the first proteins and the second proteins, and a method of measuring activated protein concentration in a cell lysate, which can quantitatively compare and measure specific activated protein concentrations in the cell of an experimental group and the cell of a control group.

BACKGROUND ART

A cell maintains a life phenomenon by performing several biological functions, such as gene expression, cell growth, cell cycle, metabolism, signal transduction, and the like, through various and complex protein-protein interactions. Accordingly, the understandings of intracellular protein-protein interactions and functions of the interactions have been the foundation of the understandings of the life phenomenon and are an essential part for developing new drugs and treating diseases.

A representative method of investigating protein-protein interactions in vitro is an affinity chromatography method.

In the case of protein affinity chromatography, it is difficult to purify a protein. In addition, since the interactions between proteins are confirmed only in vitro, it may result in false-positive results for proteins to be bound by an electrostatic interaction during passing the proteins, which are not interacted in the cell, through a column.

That is, in order to perform a quantitative measurement, a method of investigating the protein-protein interactions according to the conventional technologies analyzes the interactions in the isolation of proteins from other intracellular materials by purifying each of the proteins that exist in the cell for analyzing the protein-protein interactions. Accordingly, there is a limit to analyze the protein-protein interactions at the single molecular level in the actual intracellular environment with co-existing other proteins, and the like.

Moreover, a method of investigating the protein-protein interactions according to the conventional technologies has a problem that the degrees of effects of other proteins on specific protein-protein interactions cannot be analyzed when other proteins are involved with the interactions in the actual intracellular environment.

In addition, there was a conventional limit to compare and measure quantitatively specific activated protein concentrations in the cell of an experimental group and the cell of a control group.

SUMMARY OF THE DISCLOSURE

Accordingly, an object of the present invention is to provide a method of analyzing protein-protein interactions, which can analyze the protein-protein interactions at a single molecular level in the actual intracellular environment, as well as can compare and confirm each cell state and activation levels of first proteins by comparing after varying of a type of cells supplying the first protein for observing interactions between the first proteins and the second proteins.

Moreover, another object of the present invention is to provide a method of measuring activated protein concentrations in a cell lysate, which can compare and measure quantitatively specific activated protein concentrations in the cell of an experimental group and the cell of a control group.

To accomplish the above objects, according to one aspect of the present invention, there is provided a method of analyzing interactions between first proteins and second proteins by at a single molecular level, comprising: (a) preparing at least two substrates, in which first protein-binding molecules that are biomolecules to be bound to the first proteins are attached to each of the substrates; (b) inducing binding between the first proteins and the first protein-binding molecules on the first substrate and the second substrate, respectively, by supplying the first proteins included in the control group-cell to the first substrate among the two substrates and supplying the first proteins included in the experimental group-cell to the second substrate among the two substrates; (c) supplying cell lysates of cells including the marker-tagged second proteins to the first substrate and the second substrate, respectively, when the first proteins and the first protein-binding molecules are bound to the first substrate and the second substrate, respectively; and (d) comparing and analyzing the interactions between the first proteins and the second proteins on the first substrate and the second substrate in the supply of the cell lysates to the first substrate and the second substrate, respectively.

Preferably, in the step (b), the control group-cell is a normal cell and the experimental group-cell is a tumor cell.

Preferably, the step (d) includes measuring a fluorescent signal having a specific wavelength generated by the markers tagged to the second proteins bound to the first proteins using an optical apparatus generating a near-field.

Preferably, in the step (d), the fluorescent signal having the specific wavelength is cumulatively measured for a predetermined time period.

Preferably, in the step (d), the fluorescent signal having the specific wavelength is measured in real-time under the presence of the cell lysates supplied to the substrate.

Preferably, the step (b) includes supplying the cell lysates of the control group-cell to the first substrate and supplying the cell lysates of the experimental group-cell to the second substrate.

Preferably, the method further comprises supplying a buffer solution to the substrate before the step (c).

According to another aspect of the present invention, there is provided a method of measuring activated protein concentration in a cell lysate, comprising: (a) preparing a substrate attaching first protein-binding molecules that are biomolecules to be bound with first proteins; (b) inducing binding of the first proteins and the first protein-binding molecules by supplying the cell lysates including the first proteins to the substrate; (c) supplying the cell lysates including the marker-tagged second proteins when the first proteins are bound to the first protein-binding molecules on the substrate; and (d) analyzing interactions between the first proteins and the second proteins on the substrate.

Preferably, the method further comprises (e) repeating the steps (b) to (d) by increasing the concentration of the cell lysates including the first proteins in the step (b), by a predetermined ratio.

Preferably, the step (d) includes measuring a generation frequency of a fluorescent signal having a specific wavelength generated by the markers tagged to the second proteins bound to the first proteins in any configured observation region on the substrate.

Preferably, the first proteins that interact with the second proteins in the step (d) are activated first proteins among the first proteins bound to the first protein-binding molecules.

Preferably, the step (d) includes measuring a fluorescent signal having a specific wavelength generated by the markers tagged to the second proteins bound to the first proteins using an optical apparatus generating a near-field.

According to yet another aspect of the present invention, there is provided a method of measuring activated protein concentration in a cell lysate, comprising: (a) preparing at least two substrates, to which first protein-binding molecules that are biomolecules to be bound to first proteins are attached, respectively; (b) inducing binding between the first proteins and the first protein-binding molecules on the first substrate and the second substrate, respectively, by supplying the first proteins included in the control group-cell to the first substrate among the two substrates and supplying the first proteins included in the experimental group-cell to the second substrate among the two substrates; (c) supplying cell lysates including the marker-tagged second proteins to the first substrate and the second substrate, respectively, when the first proteins and the first protein-binding molecules are bound to the first substrate and the second substrate, respectively; and (d) comparing and analyzing the interactions between the first proteins and the second proteins on the first substrate and the second substrate in the supply of the cell lysates to the first substrate and the second substrate, respectively.

Preferably, the method further comprises (e) repeating the steps (b) to (d) while increasing the concentrations of the control group-cell lysate and the experimental group-cell lysate in the step (b), by a predetermined ratio.

Preferably, the step (d) includes comparing and measuring a generation frequency of a fluorescent signal having a specific wavelength generated by the markers tagged to the second proteins bound to the first proteins in any configured observation region on the substrate.

Preferably, the first proteins that interact with the second proteins in the step (d) are activated first proteins among the first proteins bound to the first protein-binding molecules.

Preferably, the step (d) includes measuring a fluorescent signal having a specific wavelength generated by the markers tagged to the second proteins bound to the first proteins using an optical apparatus generating a near-field.

According to the present invention, it is possible to analyze the protein-protein interactions at a single molecular level in the actual intracellular environment, as well as to compare and confirm each cell state and activation levels of first proteins by comparing after varying of a type of cells supplying the first protein for observing interactions between the first proteins and the second proteins.

Moreover, according to the present invention, it possible to provide a method of measuring activated protein concentrations in a cell lysate, which can compare and measure quantitatively specific activated protein concentrations in the cell of an experimental group and the cell of a control group.

BRIEF DESCRIPTION OF DRAWINGS

The above and other objects, features and advantages of the present invention will become more apparent to those of ordinary skill in the art by describing in detail exemplary embodiments thereof with reference to the attached drawings, in which.

DETAILED DESCRIPTION

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

With reference to the appended drawings, exemplary embodiments of the present invention will be described in detail below. To aid in understanding the present invention, like numbers refer to like elements throughout the description of the figures, and the description of the same elements will be not reiterated.

Figure 1:
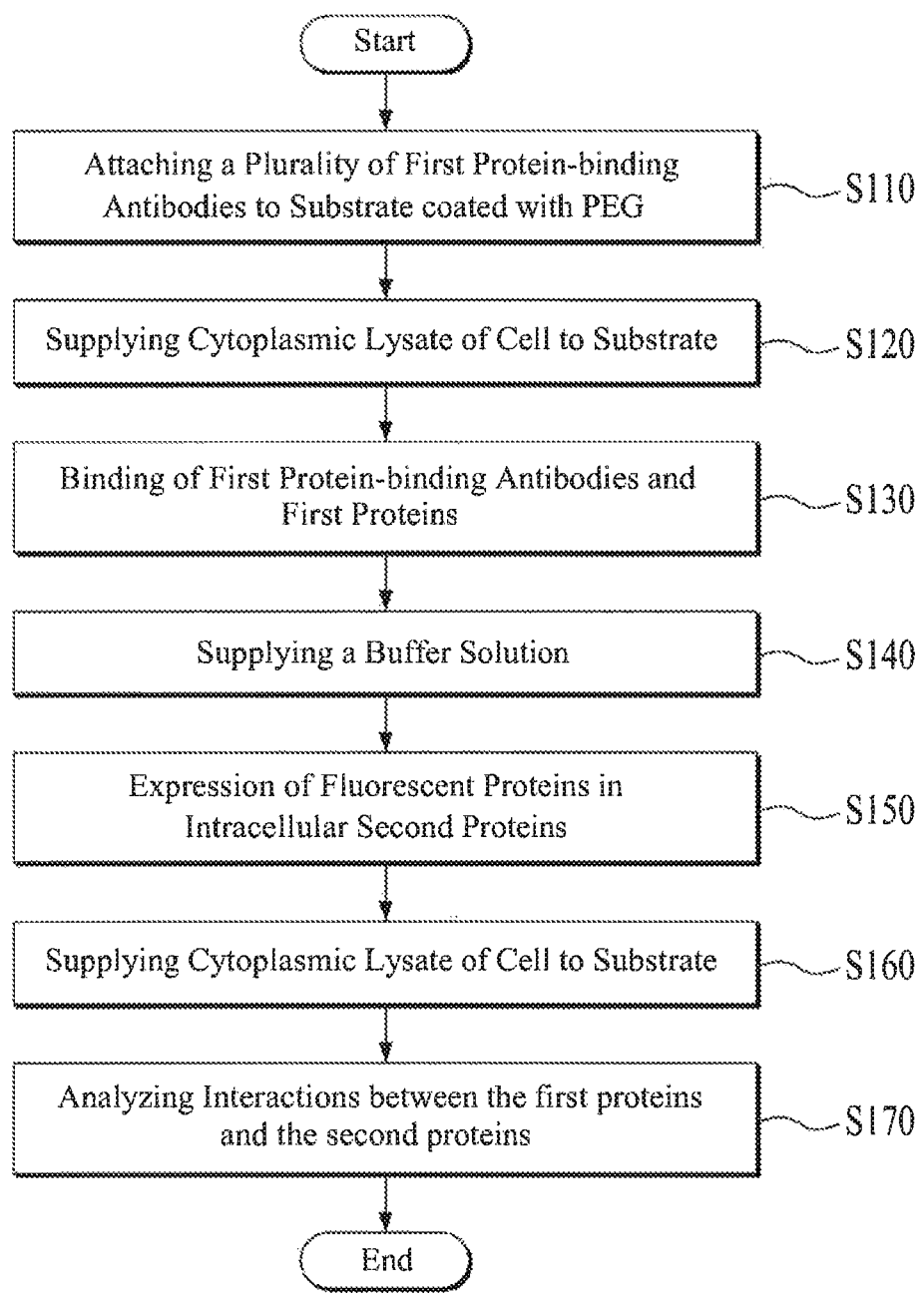
FIG. 1 is a flowchart illustrating a procedure of a method of analyzing protein-protein interactions according to an embodiment of the present invention.

FIG. 1 is a flowchart illustrating a procedure of a method of analyzing protein-protein interactions according to an embodiment of the present invention. Referring to FIG. 1, for a method of analyzing the protein-protein interactions according to an embodiment of the present invention, firstly, an analyst attaches first protein-binding antibodies (Primary antibody) that are antibodies to be bound to the first proteins to a substrate that is a quartz slide coated with polyethylene glycol (PEG), in order to analyze the interactions between the first proteins and the second proteins that are two specific proteins at a single molecular level (S110).

For the experiment according to the present invention, the first proteins are h-Ras proteins and the second proteins are Ras-binding domain (RBD) proteins of C-Raf.

Meanwhile, according to an embodiment of the present invention, the antibodies to be bound to the first proteins may include biomolecules to be bound to the first proteins, such as DNA, RNA, or liposomes having specific components to be bound to proteins, and the like, in addition to antibodies.

Subsequently, the analyst induces bindings between the first proteins and the first protein-binding antibodies by supplying (S120) cytoplasmic lysate of the cell including the first proteins to the substrate (S130).

Meanwhile, for performing the above-described step, S120, cell lysates, such as cytolysate, diluted cytoplasmic lysate, diluted or purified cytolysate, and the like, may be used in addition to the cytoplasmic lysate.

Meanwhile, according to an embodiment of the present invention, the analyst may pre-treat for an expression of predetermined first fluorescent proteins, such as m-Cherry, and the like, to the first proteins. In this case, when the first protein-binding antibodies are bound to the first proteins, the analyst may confirm whether the first proteins are bound to a plurality of first protein-binding antibodies attached on the substrate from the change of wavelength by the first fluorescent proteins that are expressed to the first proteins (i.e., measuring individual single molecule signal generated from the first fluorescent proteins) by performing an observation of the surface of the substrate using a total internal reflection fluorescence microscope.

That is, when the first fluorescent proteins are expressed in the first proteins, whether or not the first proteins are bound to the antibodies may be confirmed through the total internal reflection fluorescence microscope, and thus the number of the first proteins bound to the antibodies attached on the substrate and binding density thereof may be accurately measured.

Once confirming that the first proteins are bound to a plurality of first protein-binding antibodies attached on the substrate, respectively, the analyst removes the remaining materials included in the cytoplasmic lysate except the first proteins from the substrate by supplying a buffer solution to the substrate (S140).

Subsequently, the analyst manipulates for an expression of second fluorescent proteins through a genetic manipulation of second proteins being in different relevant cells among the same cells as the above-described cells (S150). Meanwhile, according to an embodiment of the present invention, the second fluorescent molecules may be attached or connected to the second proteins by a physical-chemical method.

Meanwhile, the above described step, S150, may be performed in advance before the above-described step, S110 in order to smoothly progress the analysis. According to an embodiment of the present invention, since the second fluorescent proteins preferably have wavelength range different from the first fluorescent proteins, when the first fluorescent proteins are m-Cherry proteins, the second fluorescent proteins may be eGFPs (enhanced Green Fluorescent Protein) that is a green fluorescent protein.

Subsequently, the analyst supplies the whole cytoplasmic lysate of the cell having the expressed second fluorescent proteins inside the second proteins from the above-described step, S150, to the substrate (S160).

At least part of the plurality of the first protein-binding antibodies attached on the surface of the substrate is bound to each first protein. When the whole cytoplasmic lysate including the second proteins is supplied to the above-described surface of the substrate as shown in FIG. 3, the first proteins (Cellular Ras) on the surface of the substrate interact with the second proteins in the same condition as the intracellular environment in the coexisting with the second proteins (eGFP-cRBD) included in the cytoplasmic lysate and native proteins in the whole cell lysate.

Figure 3:
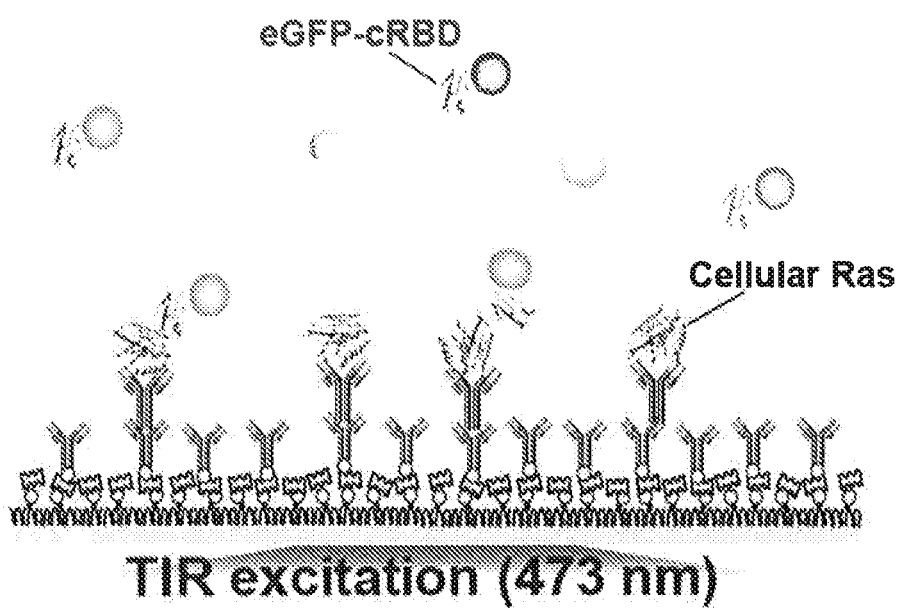

In short, as shown in FIG. 3, each first protein (Cellular Ras) bound to each antibody (Anti-Ras Primary antibody) attached on the surface of the substrate interacts with the second protein (eGFP-cRBD) in the same condition as the intracellular environment at the single molecular level thereby repeating binding and the unbinding.

Meanwhile, for performing the above-described step, S160, cell lysates, such as cytolysate, diluted cytoplasmic lysate, diluted or purified cytolysate, and the like, may be used in addition to the cytoplasmic lysate.

As shown in FIG. 3, when the first proteins are bound to the second proteins at the single molecular level, the analyst can confirm that the wavelength on the surface of the substrate is changed from 473 nm to 520 nm by eGFP that is a fluorescent protein that is expressed to the second proteins through performing an observation of substrate surface using the total internal reflection fluorescence microscope having 473 nm wavelength.

That is, the binding state between the first proteins and the second proteins can be confirmed through a detection of fluorescence signals having a specific wavelength bandwidth (520 nm) generated from the second fluorescent protein (eGFP) located on the surface of the substrate through the binding between the first proteins and the second proteins, and the analyst can analyze the interactions, such as the frequencies of binding and unbinding between the first proteins and the second proteins, and the like, at the single molecular level by continuously observing the change of wavelength at each of antibodies attached on the surface of the substrate (S170).

In addition, the interactions, such as the frequencies of the binding and unbinding between the first proteins and the second proteins, and the like, can be analyzed in the same environment as the intracellular environment by measuring the fluorescence signals having a specific wavelength in real time under the presence of the cytoplasmic lysate supplied to the substrate in the above-described step, S160.

Meanwhile, according to an embodiment of the present invention, the analyst may compare and analyze the interactions between the first proteins and the second proteins in the cell of a normal state (cell of a control group) and the interactions between the first proteins and the second proteins in cell of an abnormal state (cell of an experimental group).

Figure 4:
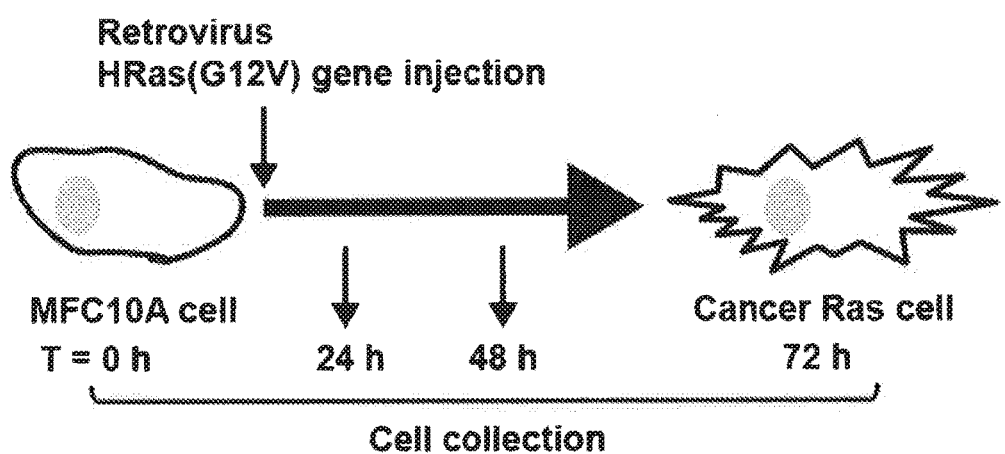
FIG. 4 is a diagram illustrating a changing process of a cell state in another embodiment of the present invention.

According to an embodiment of the present invention, a normal breast tissue cell is changed to a tumor cell as shown in FIG. 4 by artificially maximizing an activation of Ras protein in the cell isolated from a breast tissue of a human body, and the normal breast tissue cell was used as the cell of a control group and the breast tissue cell to be changed to the tumor cell was used as the cell of an experimental group.

Figure 5:
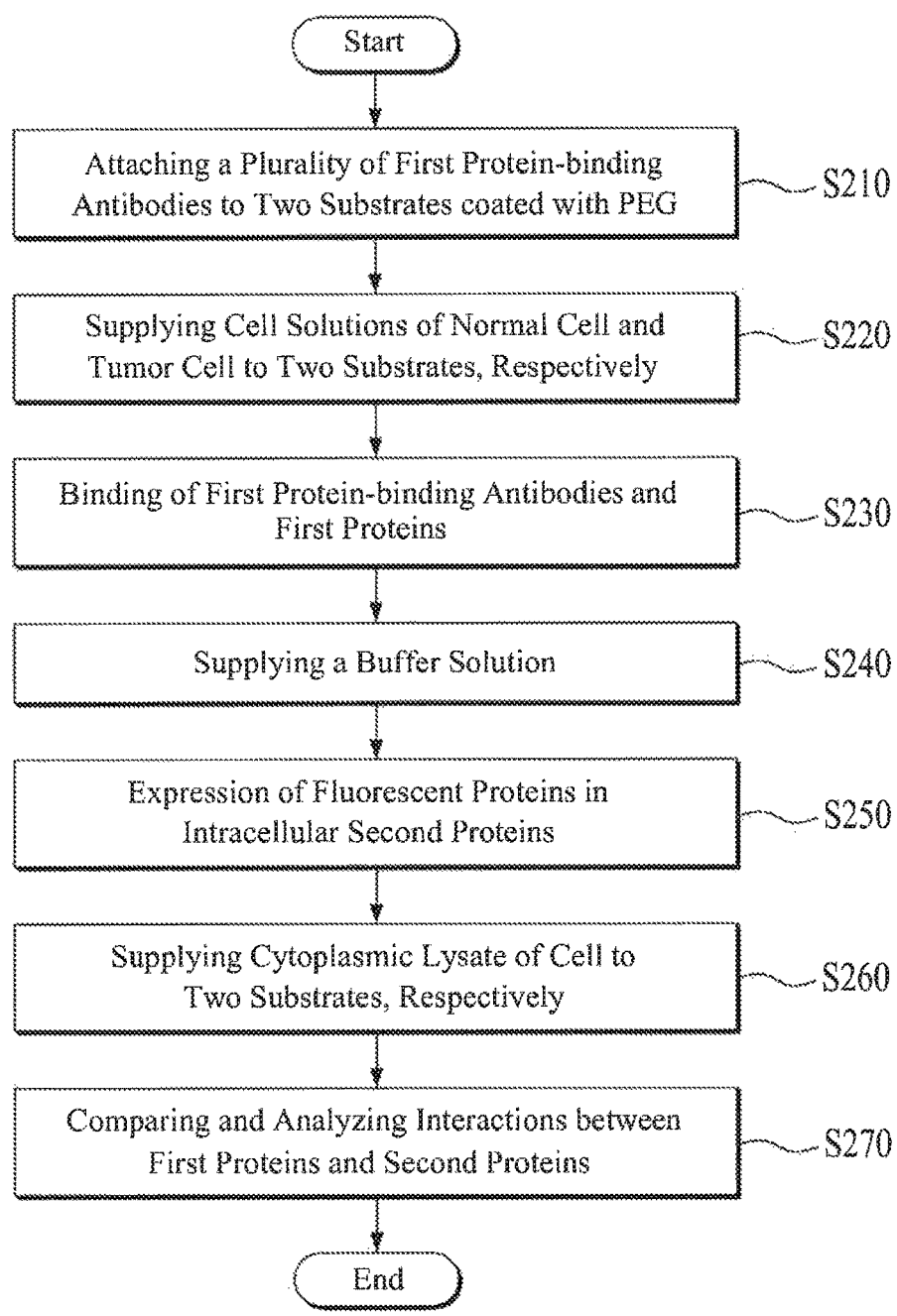
FIG. 5 is a flowchart of the procedure illustrating a method of analyzing protein-protein interactions according to another embodiment of the present invention.

FIG. 5 is a flowchart illustrating a procedure of a method of analyzing protein-protein interactions according another embodiment of the present invention. Referring to FIG. 5, for a method of analyzing the protein-protein interactions according to another embodiment of the present invention, firstly, the analyst prepares two quartz slide substrates with the same size coated with polyethylene glycol (PEG).

Figure 2:
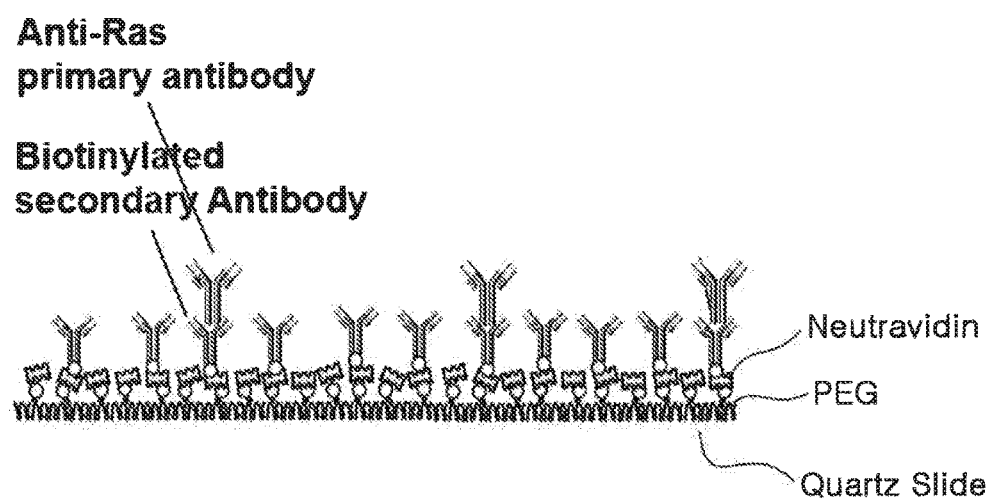
FIG. 2 to FIG. 3 are diagrams illustrating each step of a method of analyzing the protein-protein interactions according to an embodiment of the present invention.

Subsequently, the analyst attaches the first protein-binding antibodies (Anti-Ras Primary antibody) that are the antibodies to be bound to the first proteins on both of two substrates (first substrate and second substrate) as shown in FIG. 2 (S210).

Meanwhile, according to an embodiment of the present invention, the antibody to be bound to the first proteins may include biomolecules to be bound to the first proteins, such as DNA, RNA, or liposomes having specific components to be bound to proteins, and the like, in addition to antibodies.

Subsequently, the analyst induces binding between the first proteins and the first protein-binding antibodies (Anti-Ras Primary antibody) on each of the first substrate and the second substrate by supplying (S220) the cytoplasmic lysate of the cell of the control group including the first proteins to the first substrate and the cytoplasmic lysate of the cell of the experimental group including the first proteins to the second substrate (S230).

Meanwhile, according to an embodiment of the present invention, the concentration of the first proteins included in the cell of the control group should be equal to the concentration of the first proteins included in the cell of the experimental group. To achieve this, it should be confirmed whether both of the concentrations of the first proteins included in the cells of the control group and the experimental group are one and the same by measuring both of the concentrations. When both of the concentrations are not the same as each other, the above-described step, S230, should be performed after both of the concentrations are adjusted to be the same as each other through diluting, and the like.

At this time, various methods of measuring protein concentration according to the conventional technologies may be used for measuring the protein concentration, and a method of measuring protein concentration as disclosed in Korean Patent Application No. 10-2011-0088074 (Applicant, Tae-Young Yoon) may be also used. Meanwhile, the present description includes the description and figures as shown in Korean Patent Application No. 10-2011-0088074 as a part thereof.

Meanwhile, for performing the above-described step, S230, cell lysates, such as cytolysate, diluted cytoplasmic lysate, diluted or purified cytolysate, and the like, may be used in addition to the cytoplasmic lysate.

Meanwhile, according to an embodiment of the present invention, the analyst may pre-treat for an expression of predetermined first fluorescent proteins, such as m-Cherry, and the like, to the first proteins. In this case, when the first protein-binding antibodies are bound to the first proteins, the analyst may confirm whether the first proteins are bound to the plurality of the first protein-binding antibodies attached on the substrate from the change of wavelength by the first fluorescent proteins that are expressed in the first proteins (i.e., measuring single molecule signal generated from the first fluorescent proteins) by performing an observation of the surface of the substrate using the total internal reflection fluorescence microscope.

That is, when the first fluorescent proteins are expressed in the first proteins, whether or not the first proteins are bound to the antibodies may be confirmed through the total internal reflection fluorescence microscope, and thus the number of the first proteins bound to the antibodies attached on the substrate and binding density thereof may be accurately measured.

When it is confirmed that the first proteins are bound to the plurality of the first protein-binding antibodies attached on the first substrate and the second substrate, respectively, the analyst removes the remaining materials included in the cytoplasmic lysate except the first proteins from the substrates by supplying a buffer solution to the substrates (S240).

Subsequently, the analyst manipulates to express second fluorescent proteins through a genetic manipulation of second proteins that exist in specific cells (S250). Meanwhile, according to an embodiment of the present invention, the second fluorescent proteins may be attached or connected to the second proteins by a physical-chemical method.

Meanwhile, the above-described step, S250, may be performed in advance before the above-described step, S210 in order to smoothly progress the analysis. According to an embodiment of the present invention, the second fluorescent proteins may preferably have a wavelength region different from that of the first fluorescent proteins, and thus when the first fluorescent proteins are m-Cherry proteins, the second fluorescent proteins may be eGFP (enhanced Green Fluorescent Protein) that is a green fluorescent protein.

Subsequently, the analyst supplies the whole cytoplasmic lysates of the cell with the expressed second fluorescent proteins inside the second proteins in the above-described step, S260, to the first substrate and the second substrate, respectively (S260).

Meanwhile, for performing the above-described step, S260, the concentration of the second proteins in the cytoplasmic lysates to be supplied to the first substrate and the second substrate, respectively, should be the same as each other. To achieve this, it should be confirmed whether both of the concentrations of the second proteins included in two cytoplasmic lysates are one and the same by measuring both of the concentrations. When both of the concentrations are not the same as each other, the above-described step, S260, should be performed after both of the concentrations are adjusted to be the same as each other through diluting, and the like.

At this time, various methods of measuring protein concentration according to the conventional technologies may be used for measuring the protein concentration, and a method of measuring protein concentration as above-disclosed in Korean Patent Application No. 10-2011-0088074 (Applicant, Tae-Young Yoon) may be also used.

Meanwhile, for performing the above-described step, S220, cell lysates, such as cytolysate, diluted cytoplasmic lysate, diluted or purified cytolysate, and the like, may be used in addition to the cytoplasmic lysate.

The first proteins of the cell of the control group and the first proteins of the cell of the experimental group are bound to the plurality of the first protein-binding antibodies that are attached to the surfaces of the first substrate and the second substrate, respectively. When the whole cytoplasmic lysate including the second proteins on the above-mentioned surface of the substrate are supplied as shown in FIG. 3, the first proteins on each surface of the substrates interact with the second proteins in the same state as the intracellular environment that co-exists with the second proteins (eGFP-cRBD) included in the cytoplasmic lysate and native proteins in the whole cell lysate.

The analyst may confirm binding state of the first proteins and the second proteins through a detection of the fluorescent signal having a specific wavelength bandwidth (520 nm) generated from the second fluorescent protein (eGFP) to be located on the surface of the substrate through binding between the first proteins and the second proteins, and may compare and analyze the interactions, such as the frequencies of binding and unbinding between the first proteins and the second proteins on the first substrate and the second substrate, and the like, by continuously observing the change of wavelength of each antibody attached on the surface of the substrate (S270).

Figure 6:
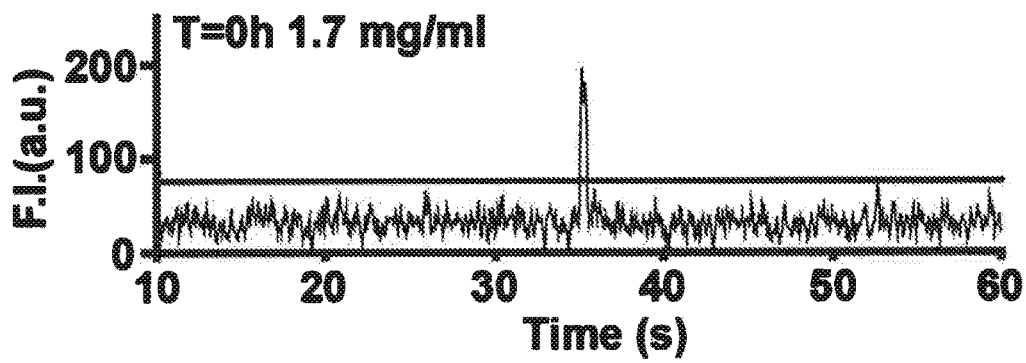
FIG. 6 is a graph showing signals observed at a first substrate binding first proteins in the cell of a control group.
Figure 7:
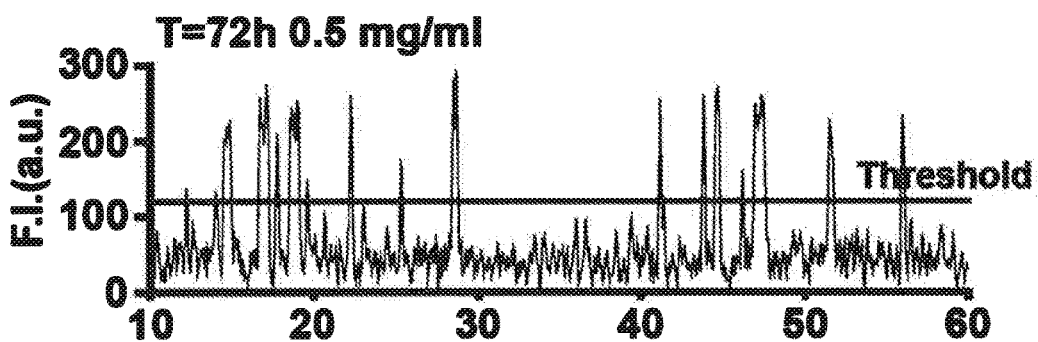
FIG. 7 is a graph showing signals observed at a second substrate binding first proteins in the cell of an experimental group.

FIG. 6 is a graph showing the signal observed on the first substrate bound with the first proteins in the cell of the control group and FIG. 7 is a graph showing the signal observed on the second substrate bound with the first proteins in the cell of the experimental group.

Comparing between FIG. 6 and FIG. 7, it may be confirmed that the interaction between the first proteins and the second proteins in the cell of the experimental group, that is a tumor cell, is more active as compared with the interaction between the first proteins and the second proteins in the cell of the control group, that is a normal cell. From this, the analyst may confirm that Ras protein that is the first protein in the tumor cell is excessively activated Meanwhile, the first proteins interacting with the second proteins may become to be the activated first proteins, and thus the activation levels of the first proteins in the cell of a control group and the first proteins in the cell of a experimental group may be quantitatively measured by comparing the interactions between the first proteins and the second proteins in the cell of the control group and the interactions between the first proteins and the second proteins in the cell of the experimental group as mentioned above.

Figure 8:
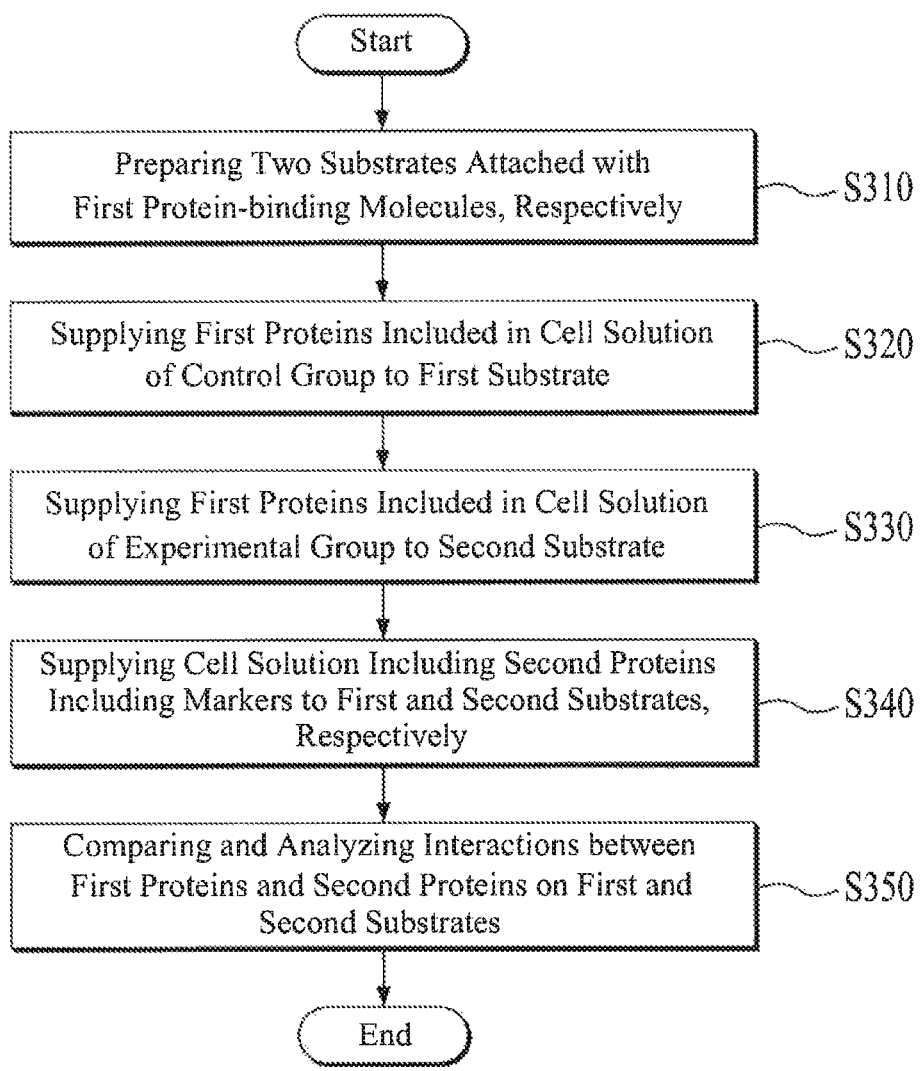
FIG. 8 is a diagram illustrating a method of comparing activated protein concentrations in the cell of a control group and the cell of an experimental group according to another embodiment of the present invention.

To achieve this, the present invention uses the method as shown in FIG. 8. FIG. 8 is a diagram illustrating a method of comparing the activated protein concentrations in the cells of a control group and an experimental group according to another embodiment of the present invention.

Referring to FIG. 8, the analyst prepares two quartz slide substrates with the same size coated with polyethylene glycol (PEG) and attaches the first protein-binding antibodies (Anti-Ras Primary antibody) that are antibodies to be bound to each first protein to two substrates (first substrate and second substrate) as shown in FIG. 2 (S310).

Subsequently, the analyst induces binding between the first proteins and the first protein-binding antibodies (Anti-Ras Primary antibody) on each of the first substrate and the second substrate, respectively, by supplying (S320) the cell lysates of the control group-cell including the first proteins to the first substrate and supplying (S330) the cell lysates of the experimental group-cell including the first proteins to the second substrate.

Meanwhile, according to an embodiment of the present invention, the concentration of the first proteins included in the cell of the control group should be equal to the concentration of the first proteins included in the cell of the experimental group. To achieve this, it should be confirmed whether both of the concentrations of the first proteins included in the cells of the control group and the experimental group are one and the same by measuring both of the concentrations.

When both of the concentrations are not the same as each other, the above-described steps, S320 to S220, should be performed after both of the concentrations are adjusted to be the same as each other through diluting, and the like.

At this time, various methods of measuring protein concentration according to the conventional technologies may be used for measuring the protein concentration, and a method of measuring protein concentration as above-disclosed in Korean Patent Application No. 10-2011-0088074 (Applicant, Tae-Young Yoon) may be also used.

Meanwhile, according to an embodiment of the present invention, the analyst may pre-treat for an expression of predetermined first fluorescent proteins, such as m-Cherry, and the like, to the first proteins. In this case, when the first protein-binding antibodies are bound to the first proteins, the analyst may confirm whether the first proteins are bound to the plurality of the first protein-binding antibodies attached on the substrate from the change of wavelength by the first fluorescent proteins that are expressed to the first proteins (i.e., measuring single molecule signal generated from the first fluorescent proteins) by performing an observation of the surface of the substrate using the total internal reflection fluorescence microscope.

That is, when the first fluorescent proteins are expressed in the first proteins, whether the first proteins are bound to the antibodies may be confirmed through the total internal reflection fluorescence microscope, and thus the number of the first proteins bound to the antibodies attached on the substrate and binding density thereof may be accurately measured.

When it is confirmed that the first proteins are bound to the plurality of the first protein-binding antibodies attached on the first substrate and the second substrate, respectively, the analyst removes the remaining materials included in the cytoplasmic lysate except the first proteins from the substrates by supplying a buffer solution to the substrates.

Subsequently, the analyst manipulates to express second fluorescent proteins through a genetic manipulation of second proteins that exist for specific cells. Meanwhile, according to an embodiment of the present invention, the second fluorescent proteins may be attached or connected to the second proteins by a physical-chemical method.

Meanwhile, according to an embodiment of the present invention, the second fluorescent proteins may preferably have a wavelength region different from that of the first fluorescent proteins, and thus when the first fluorescent proteins are m-Cherry proteins, the second fluorescent proteins may be eGFP (enhanced Green Fluorescent Protein) that is a green fluorescent protein.

Subsequently, the analyst supplies the whole cell lysate of the cell with the expressed second fluorescent proteins inside the second proteins to the first substrate and the second substrate, respectively (S340).

Meanwhile, for performing the above-described step, S340, the concentration of the second proteins in the cell lysate to be supplied to the first substrate and the second substrate, respectively, should be the same as each other. To achieve this, it should be confirmed whether both of the concentrations of the second proteins included in two cytoplasmic lysates are one and the same by measuring both of the concentrations. When both of the concentrations are not the same as each other, the above-described step, S340, should be performed after both of the concentrations are adjusted to be the same as each other through diluting, and the like.

At this time, various methods of measuring protein concentration according to the conventional technologies may be used for measuring the protein concentration, and a method of measuring protein concentration as above-disclosed in Korean Patent Application No. 10-2011-0088074 (Applicant, Tae-Young Yoon) may be also used.

The first proteins of the cell of the control group and the first proteins of the cell of the experimental group are bound to the plurality of the first protein-binding antibodies that are attached to the surfaces of the first substrate and the second substrate, respectively. When the whole cell lysates, such as the cytoplasmic lysate including the second proteins on the above-mentioned surface of the substrate, and the like, are supplied as shown in FIG. 3, the first proteins on each surface of the substrates interact with the second proteins in the same state as the intracellular environment that allows for the coexistence of the second proteins (eGFP-cRBD) included in the cytoplasmic lysate and native proteins in the whole cell lysate.

The analyst may confirm binding state of the first proteins and the second proteins through a detection of the fluorescent signal having a specific wavelength bandwidth (520 nm) generated from the second fluorescent protein (eGFP) to be located on the surface of the substrate through binding between the first proteins and the second proteins, and may compare and analyze the interactions, such as the frequencies of binding and unbinding between the first proteins and the second proteins on the first substrate and the second substrate, and the like, by continuously observing the change of wavelength to each antibody attached on the surface of the substrate (S350).

More specifically, the analyst repeats the above-described steps, S320 to S350, while gradually and equally increasing the concentration of the first proteins included in the cell lysate of the control group and the concentration of the first proteins included in the cell of the experimental group supplied to the first substrate and the second substrate in the above-described steps, S320 and S330.

Figure 9:
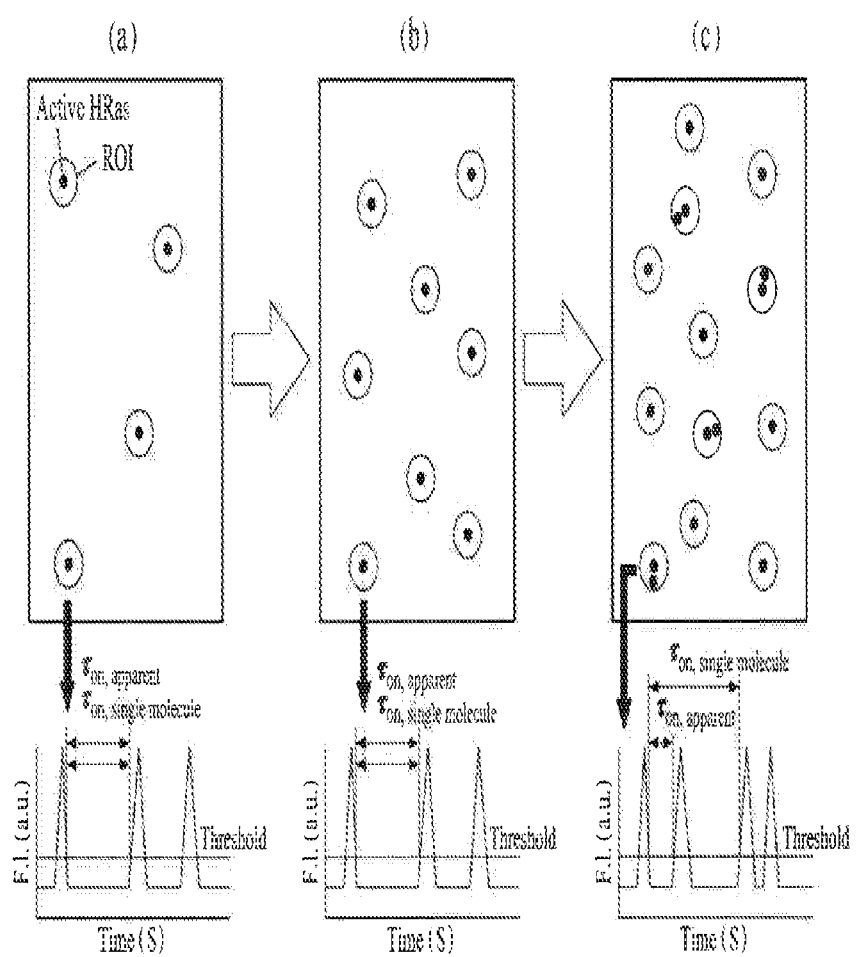
FIG. 9 is a diagram showing an experimental result of measuring interactions between first proteins and second proteins while gradually increasing the concentrations of the first proteins included in the cell of an experimental group.

FIG. 9 is a diagram showing the experimental results of measuring the interaction between the first proteins and the second proteins with gradually increasing the concentration of the first proteins included in the cell of the experimental group. Referring to FIG. 9(a), the cell lysate of the cell of the experimental group including the first proteins (HRas) of 1 nM concentration is supplied to the second substrate to induce binding between the first proteins and the first protein-binding molecules and then the generated signal of the fluorescent signal having a specific wavelength generated by markers tagged to the second proteins is measured by using an optical apparatus generating a near-field in the supply of the cell lysates including the marker-tagged second proteins to the second substrate.

Specifically, since only activated first proteins among the first proteins bound to the first protein-binding molecules attached to the second substrate interact with the second protein, for measuring using the above-described optical apparatus, the optical apparatus can measure a frequency of fluorescent signal generation with each ROI (Region of Interest) as the center after setting ROI of any 1.1 μm² size with the point of sensing the fluorescent signal having a specific wavelength that exceeds a predetermined threshold as the center.

Meanwhile, referring to FIG. 9(b), the cell lysate of the cell of the experimental group including the first proteins (HRas) of 2 nM concentration is supplied to the second substrate to induce binding between the first proteins and the first protein-binding molecules and then the generated signal of the fluorescent signal with a specific wavelength generated by a marker tagged to the second proteins is measured by using an optical apparatus generating a near-field in the supply of the cell lysate including the marker-tagged second proteins to the second substrate.

Specifically, since only activated first proteins among the first proteins bound to the first protein-binding molecules attached to the second substrate interact with the second protein, when the concentration of the cell lysate of the cell of the experimental group including the first proteins is increased by two times, the point of sensing the fluorescent signal of a specific wavelength that exceeds a predetermined threshold is observed by two times as compared with FIG. 9(a) (Four ROI→Eight ROI).

Meanwhile, since the concentration of the cell lysate of the experimental group-cell is not still relatively high, only one of pairs of the interactions between the activated first proteins and second proteins in one ROI having a certain size is being observed.

Accordingly, the frequency of the fluorescent signal generation averagely measured in eight ROI in FIG. 9(b) is equal to that of FIG. 9(a).

However, since a configurable number of ROI according to the size of the second substrate is limited, when the concentration of the experimental group-cell lysate including the first proteins exceeds at least a threshold, at least two pairs of the interactions between activated first proteins and second proteins are observed in one ROI as shown in FIG. 9(c).

When the concentration of the experimental group-cell lysate exceeds a threshold as mentioned above, the average value of the frequency of the fluorescent signal generation becomes to increase in each ROI and then the average value of the frequency of the fluorescent signal generation is continuously increased with an increasing concentration of the experimental group-cell lysate, continuously.

According to an embodiment of the present invention, when the sizes of the first substrate and second substrate are 45×90 μm², the threshold of the experimental group-cell lysate of the tumor cell including the first proteins (HRas), in which the average value of the frequency of the fluorescent signal generation is started to increase in each ROI with the size of 1.1 μm², is measured to be 5 nM.

Figure 10:
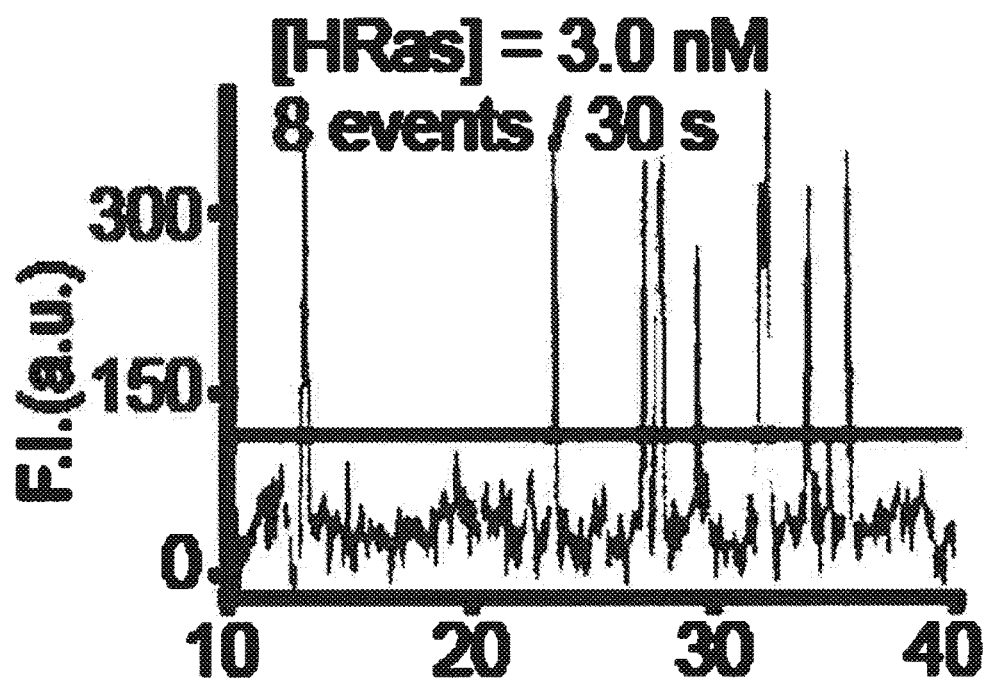
FIG. 10 and FIG. 11 are graphs showing measurements of fluorescent signals measured with increasing concentrations of the first proteins included in the cell of an experimental group.
Figure 11:
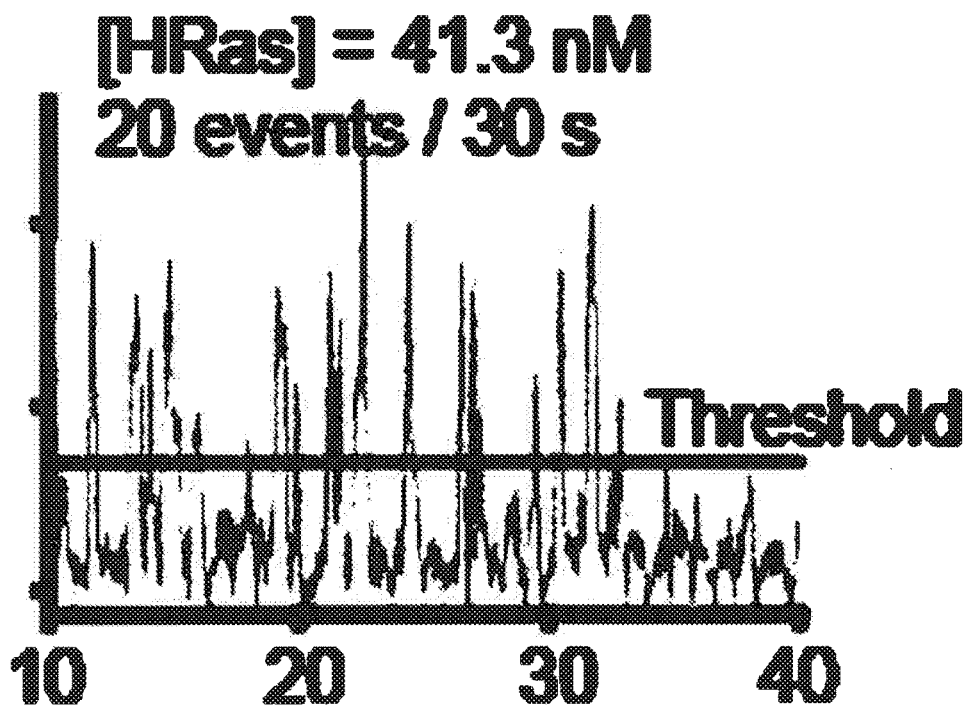

That is, as confirmed in FIG. 10, the cell lysate of the experimental group-cell including the first proteins (HRas) with 3 nM concentration is supplied to the second substrate to induce binding between the first proteins and the first protein-binding molecules. From that point, when the frequency of the fluorescent signal generation with specific wavelength generated by the markers tagged to the second proteins is measured by using an optical apparatus in a plurality of ROIs as its average value in the supply of the cell lysate including the marker-tagged second proteins to the second substrate, the frequency of the fluorescent signal generation is just 8 times in 30 seconds.

However, as confirmed in FIG. 1, the cell lysate of the experimental group-cell including the first proteins (HRas) with 41.3 nM concentration that exceeds a threshold concentration (5 nM) is supplied to the second substrate to induce binding between the first proteins and the first protein-binding molecules. From that point, when the frequency of the fluorescent signal generation with a specific wavelength generated by a marker tagged to the second proteins is measured by using an optical apparatus generating a near-field in a plurality of ROIs as its average value in the supply of the cell lysate including the marker-tagged second proteins to the second substrate, the frequency of the fluorescent signal generation is measured to be 20 times in 30 seconds.

Figure 14:
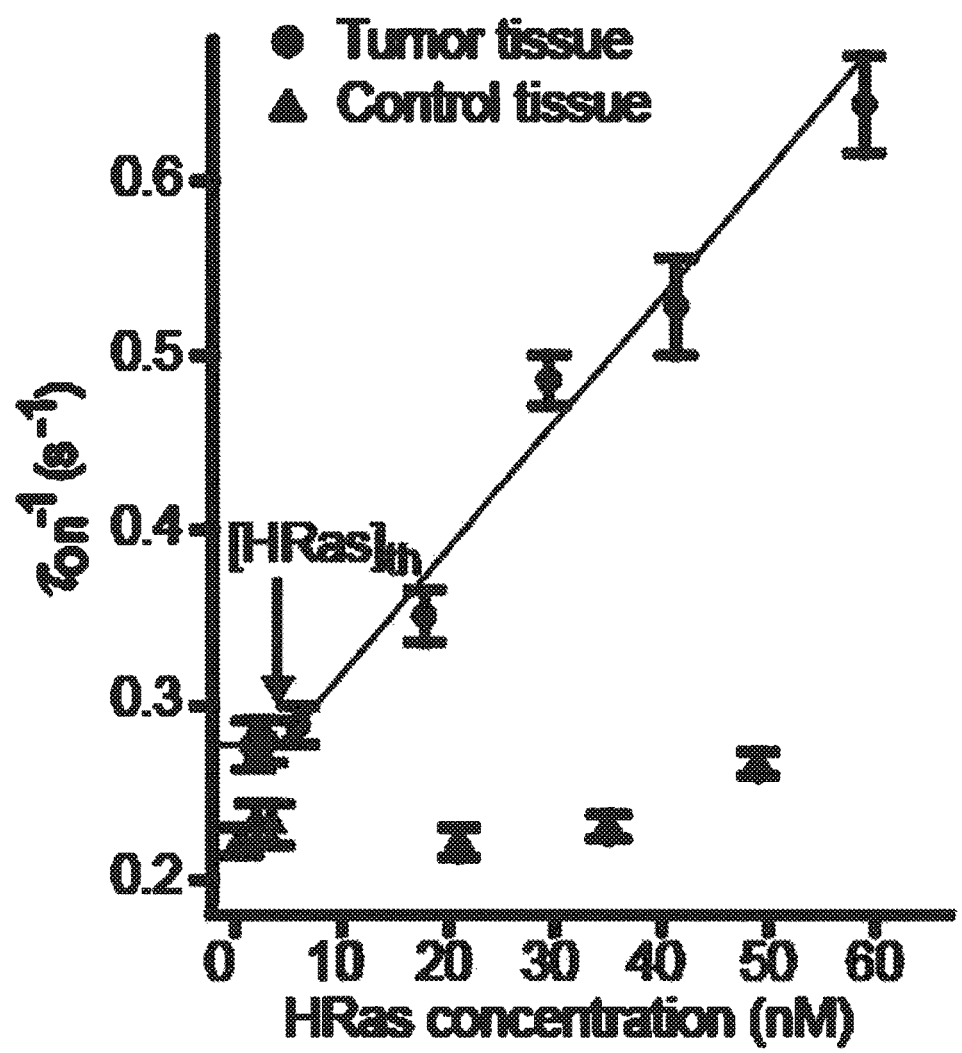
FIG. 14 is a graph showing comparisons of changes of frequencies measured with increasing concentrations of the first proteins in the cell of an experimental group and the cell of a control group, respectively.

That is, while increasing the concentration value of the cell lysate of the experimental group-cell that is a tumor cell including the first proteins (HRas), the average value of the frequency of the fluorescent signal in a plurality of ROIs is measured. As a result, as shown in FIG. 14, it has been seen that it is constantly maintained at 5 nM that is a threshold concentration value, and then increased after exceeding the threshold concentration value.

Based on the threshold concentration value as mentioned above, the analyst may calculate the ratio of activated first proteins among the first proteins included in the cell lysate of the experimental group-cell.

In addition, the analyst may quantitatively calculate the ratio of activated first protein concentration included in the cell of the control group and the activated first protein concentration included in the cell of the experimental group by comparing the threshold concentration values in the control group-cell and the experimental group-cell by repeating the experiments as mentioned above in the control group-cell.

That is, the analyst measures the threshold concentration value in the control group-cell under the same condition while slowly increasing the concentration of the cell lysate of the control group-cell including the first proteins (HRas) along with the experimental procedure as mentioned above, or before and after the experimental procedure to the experimental group-cell in order to achieve the threshold concentration value in the experimental group-cell.

Meanwhile, for increasing the concentration of the cell lysate in the control group-cell, it is preferable to increase in the same ratio as the ratio of increasing the concentration of the cell lysate in the experimental group-cell.

Figure 12:
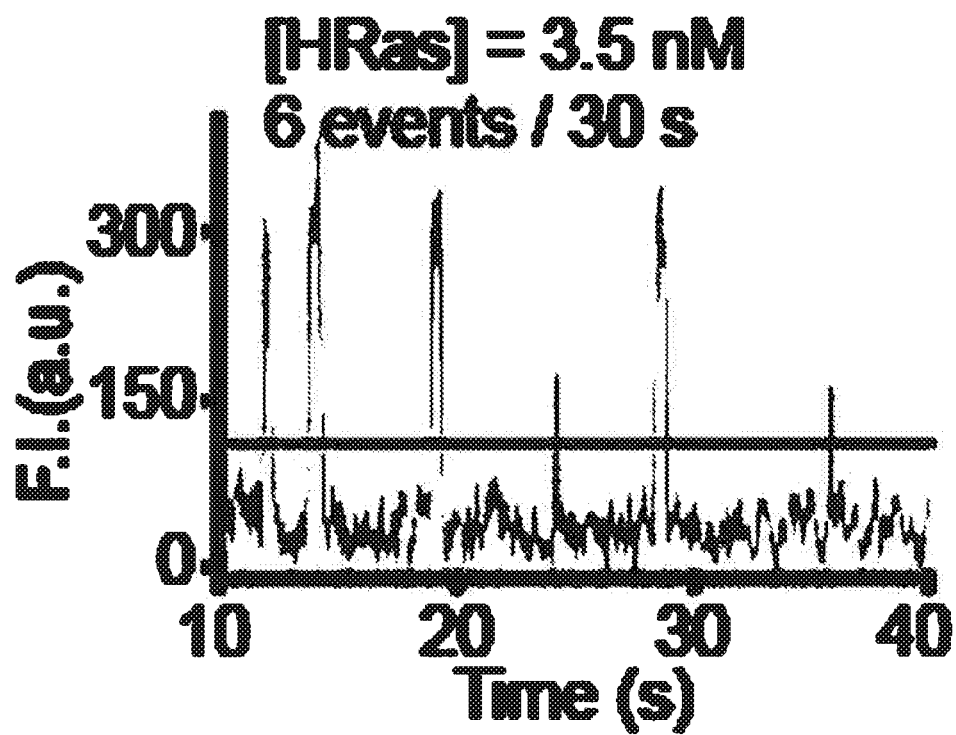
FIG. 12 and FIG. 13 are graphs showing measurements of fluorescent signals measured with increasing concentrations of the first proteins included in the cell of a control group.

That is, referring to FIG. 12, the analyst induces binding between the first proteins and the first protein-binding molecules by supplying the cell lysate of the control group-cell including the first proteins (HRas) with 3.5 nM concentration to the second substrate. From that point, when the frequency of the fluorescent signal generation having a specific wavelength generated by the markers tagged to the second proteins is measured by using an optical apparatus generating a near-field in a plurality of ROIs as its average value in the supply of the cell lysate including the marker-tagged second proteins to the second substrate, the frequency of the fluorescent signal generation is just 6 times in 30 seconds.

Meanwhile, from that point, when increasing the concentration of the cell lysate of the control group-cell, the frequency of the fluorescent signal generation measured in a plurality of ROIs as its average value is constant at 6 times in 30 seconds.

Figure 13:
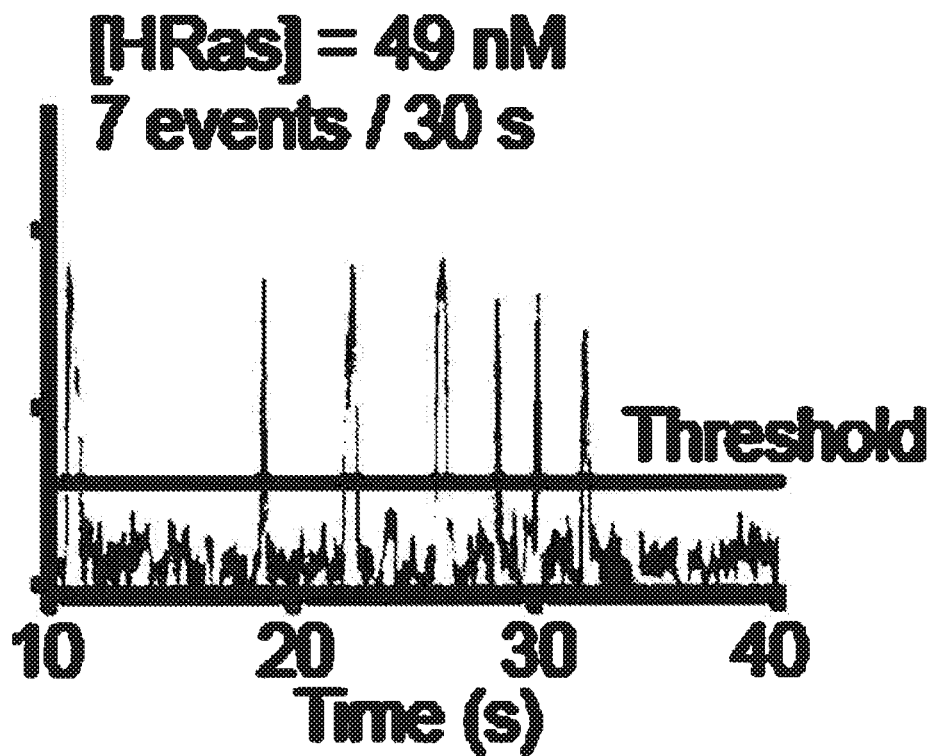

However, as confirmed in FIG. 13, the cell lysate of the control group-cell including the first proteins (HRas) with 49 nM concentration is supplied to the second substrate to induce binding between the first proteins and the first protein-binding molecules. From that point, when the frequency of the fluorescent signal generation with a specific wavelength generated by a marker tagged to the second proteins is measured by using an optical apparatus generating a near-field in a plurality of ROIs as its average value in the supply of the cell lysate including the marker-tagged second proteins to the second substrate, the frequency of the fluorescent signal generation is measured to be 7 times in 30 seconds, that is increased.

From that point, while increasing the concentration of the control group-cell lysate, the average value of a frequency of the fluorescent signal is measured. As a result, as confirmed in FIG. 14, it has been seen that it is distinctly increased after exceeding the threshold concentration value that is a 50 nM concentration.

From the above experimental results, it has been seen that the analyst can confirm the fact that the activated first proteins included in the experimental group-cell that is a tumor cell are 10 times larger than those of the activated first proteins included in the control cell that is a normal cell based on the fact that the threshold concentration value in the experimental group-cell is measured to be 5 nM and the threshold concentration value in the control group-cell is measured to be 50 nM.

According to the present invention, each cell state and activation levels of first proteins can be compared and confirmed by comparing after varying of a type of cells supplying the first proteins for observing interactions between the first proteins and the second proteins.

Moreover, according to the present invention, the protein-protein interactions can be analyzed at a single molecular level in the actual intracellular environment.

Moreover, according to the present invention, specific activated protein concentrations can be quantitatively measured in the cell of an experimental group and the cell of a control group.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A method of analyzing protein interactions between first proteins and second proteins, comprising:
   (a) preparing at least two substrates including first substrate and second substrate, in which first protein-binding molecules that are biomolecules to be bound to the first proteins are attached to each of the substrates;
   (b) inducing binding between the first proteins and the first protein-binding molecules on the first substrate and the second substrate, respectively, by supplying the first proteins as a control group to the first substrate and supplying the first proteins as an experimental group to the second substrate;
   (c) supplying cell lysates including the second proteins tagged with markers to the first substrate and the second substrate, respectively; and
   (d) comparing and analyzing the interactions between the first proteins and the second proteins on the first substrate and the second substrate by measuring a fluorescent signal having a specific wavelength generated by each of the markers tagged to the second proteins bound to the control group-first proteins and the experimental-group first proteins, respectively, using an optical apparatus generating a near-field, wherein the fluorescent signal is measured cumulatively for a predetermined integral time period.

2. The method of claim 1, wherein in the step (b), the control group-first proteins are normal cells and the experimental group-first proteins are tumor cells.

3. The method of claim 1, wherein in the step (d), the fluorescent signal having the specific wavelength is measured in real-time under the presence of the cell lysates supplied to the substrate.

4. The method of claim 1, wherein the step (b) includes supplying cell lysates including the control-group first proteins to the first substrate, and supplying cell lysates including the experimental-group first proteins to the second substrate.

5. The method of claim 1, further comprising supplying a buffer solution to the substrate before the step (c).

6. The method of claim 1, further comprising (e) repeating the steps (b) to (d) while increasing the concentrations of the control group-first proteins and the experimental group-first proteins in the step (b), by a predetermined ratio.

7. The method of claim 6, wherein the step (d) includes comparing and measuring a frequency of a fluorescent signal having a specific wavelength generated by the markers tagged to the second proteins bound to the first proteins in any configured observation region on the substrate.

8. The method of claim 1, wherein the first proteins that interact with the second proteins in the step (d) are activated first proteins among the first proteins bound to the first protein-binding molecules.

9. The method of claim 1, wherein the step (d) further includes determining frequencies of binding and unbinding between the first proteins and the second proteins.

10. The method of claim 1, wherein the step (d) further includes determining a duration of forming one binding between the first proteins and the second proteins and a time required for forming a following binding between the first proteins and the second proteins.

11. The method of claim 1, wherein the first proteins are h-Ras proteins, the second proteins are Ras-binding domain (RBD) proteins of C-Raf, the biomolecules and the first protein-binding molecules are antibodies, DNA, RNA or liposome having a specific components to be bound to the first proteins, and the substrate is a quartz slide coated with polyethylene glycol.

* * * * *